United States Patent [19]

Kelman

[11] Patent Number: 4,463,457
[45] Date of Patent: Aug. 7, 1984

[54] INTRAOCULAR LENS AND METHOD OF POSITIONING THE SAME IN AN EYE

[76] Inventor: Charles D. Kelman, 269-70 Grand Central Pkwy., Floral Park, N.Y. 11005

[21] Appl. No.: 422,373

[22] Filed: Sep. 24, 1982

[51] Int. Cl.³ .............................. A61F 1/16; A61F 1/24
[52] U.S. Cl. ............................................... 3/13; 427/2
[58] Field of Search ................................. 3/13; 427/2

[56] References Cited

U.S. PATENT DOCUMENTS 4,174,543 11/1979 Kelman ..................................... 3/13
4,240,163 12/1980 Galin ......................................... 3/13

OTHER PUBLICATIONS

Lens Implantation (Book) by P. Leonard et al., Dr W. Junk Publishers, Printed in Belgium, 1982, pp. 448-449.

Primary Examiner—Ronald L. Frinks
Attorney, Agent, or Firm—Henry Sternberg

[57] ABSTRACT

An intraocular lens and method of positioning the same in an eye in which the lens includes a layer of material which is soluble in the eye for stiffening the position-fixation members of the lens during insertion thereof into the eye.

10 Claims, 3 Drawing Figures

INTRAOCULAR LENS AND METHOD OF POSITIONING THE SAME IN AN EYE

This invention relates to intraocular lenses for the human eye and, more particularly, to intraocular lenses of the type which can be positioned in the anterior chamber, the posterior chamber, or partially in anterior chamber and partially in the posterior chamber of the eye. The invention also relates to methods of positioning such lenses in an eye.

One type of intraocular lens is described and claimed in my U.S. Pat. No. 4,174,543 issued Nov. 20, 1979. Such a lens includes a lens body and position-fixation means extending therefrom. The lens is inserted into the eye through a corneo-scleral incision. To minimize the possibility of injury to the eye, the position-fixation means may comprise a pair of flexible members which easily bend. To facilitate insertion of such members into the eye, it is desirable that they exhibit greater stiffness during the insertion procedures. However, the flexibility and resilience of the position-fixation members is necessary so that they do not exert excessive pressure in the regions of the eye where they are positioned and seated by the surgeon after insertion.

It is an object of the present invention, therefore, to provide a new and improved intraocular lens which avoids one or more of the limitations of prior such lenses.

It is another object of the invention to provide a new and improved intraocular lens which is stiffened during insertion into the eye and is more flexible after insertion into the eye.

It is another object of the invention to provide a new and improved method of positioning an intraocular lens in an eye which avoids one or more of the limitations of prior such methods.

In accordance with the invention, an intraocular lens comprises a lens body and position-fixation means extending from the lens body and having a portion remote from the lens body for positioning the lens body within an eye. The lens also includes a layer of material which is soluble in the eye extending from the lens body to the remote portion of the position-fixation means, thereby stiffening the position-fixation means during insertion thereof into the eye.

Also in accordance with the invention, a method of positioning an intraocular lens in an eye, the lens comprising a lens body and position-fixation means extending from the lens body and having a portion remote from the lens body for positioning the lens body within the eye, comprises applying to the lens a layer of material which is soluble in the eye extending from the lens body to the remote portion of the position-fixation means to stiffen the lens. The method also includes inserting the lens into the eye through an opening in the eye and seating the lens in the eye.

For a better understanding of the present invention together with other and further objects thereof, reference is made to the following description, taken together with the accompanying drawings, and its scope will be pointed out in the appended claims.

Referring now to the drawings.

Figure 1:
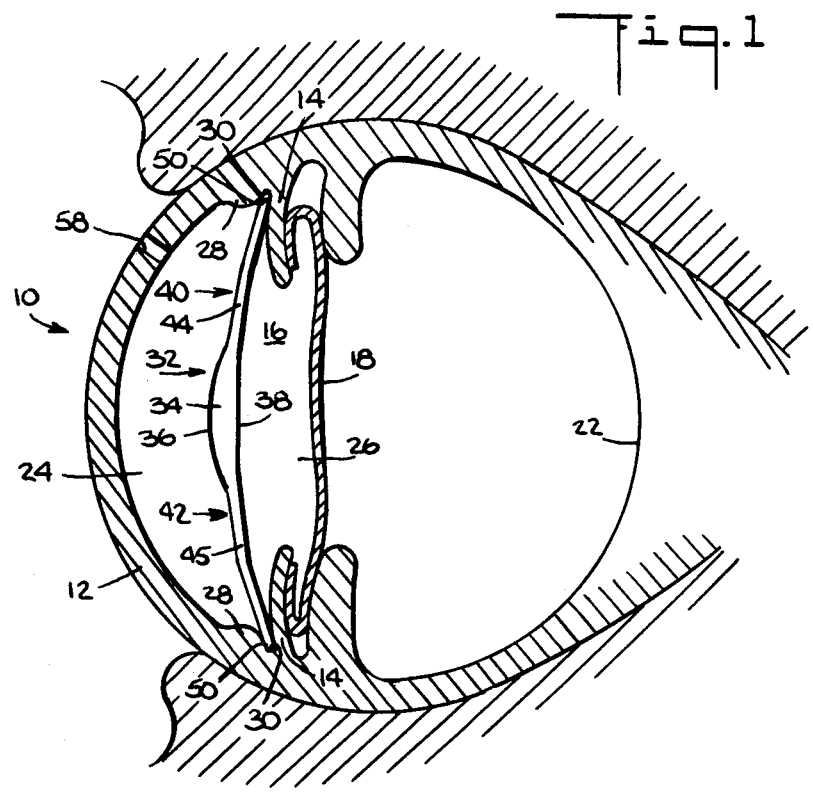
FIG. 1 is a simplified schematic sectional view of an eyeball implanted with an intraocular lens embodying one form of the present invention.
Figure 2:
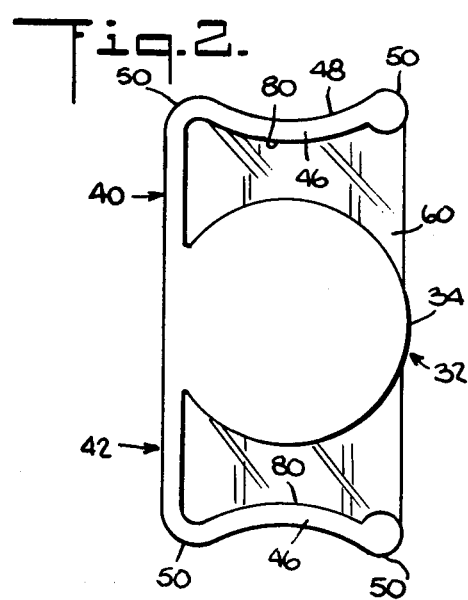
FIG. 2 is a plan view of the intraocular lens represented in FIG. 1.

Referring now more particularly to FIGS. 1 and 2 of the drawings, reference numeral 10 generally designates an eyeball as shown in simplified schematic cross-section in FIG. 1. Portions of the eyeball structure which are not believed to be essential to an understanding of the invention have been omitted for the sake of clarity.

The eyeball 10 includes a cornea 12, an iris 14 having a central opening or pupil 16, a posterior capsule 18 and a retina 22. The natural lens, which is normally held in the capsule 18, has been omitted since the invention deals with artificial substitutes for a natural lens. An aqueous zone, between the cornea 12 and the membrane 18, is subdivided by the iris 14 into an anterior chamber 24 and a posterior chamber 26. A scleral spur 28 in the anterior chamber 24 is spaced from the iris 14 thereby defining a groove 30.

An intraocular artificial lens for the eyeball 10 is generally indicated by reference numeral 32 in FIG. 1 and will first be described generally with reference to FIGS. 1 and 2. The lens 32 can be formed of any suitable material which is compatible with the environment of the eyeball, such as a non-toxic plastic, for example, polymethylmethacrylate.

The lens 32 includes a light-focusing lens body 34 or optic having, for example, a convex anterior surface 36 and a generally flat posterior surface 38. Position-fixation means comprise, for example, a pair of oppositely disposed symmetrical position-fixation members 40 and 42 which include respective stem portions 44 and 45 that extend from the periphery of the lens body 34.

The stem portions 44 and 45 individually have identical limb portions 46, 46 joined thereto in cantilever arrangement and extending transversely thereof and remote from the lens body 34. A concave outer seating edge 48 of each of the limb portions 46, 46 terminates with respective contact lobes 50, 50. With this arrangement an inner edge portion 80 of each limb portion 46 is free from contact with the periphery of the lens body 34. The lens body portion 34 may, for example, have a diameter of 5 mm and a thickness of 0.4 mm. For example, the thickness of each of the position-fixation members 40 and 42 may be 0.2 mm and the width thereof about 1.2 mm. The distance between corresponding contact lobes 50, 50 from one of the members 40, 42 to the other may be, for example, about 12 mm. The radius of curvature of the concave outer seating edge 48 of each member 40, 42 may be, for example, approximately 180 mm.

The limb portions 46, 46 of the position-fixation members 40, 42 are preferably slightly inclined with respect to the plane of the posterior surface 38 of the lens body and seat in the anterior angle or groove 30 as shown in FIG. 1. The posterior surface 38 of the lens body 34 lies in a plane that is preferably substantially coplanar with the plane of the stem portions 44, 45 and is spaced from a plane containing the outer edges of the lobes 50 by about 0.25 mm to 0.75 mm. This spacing is desirable to maintain the lens body 34 out of contact with the iris and to prevent the lens from interfering with expansion and contraction of the pupil 16.

Referring now more particularly to FIG. 2 of the drawings, the lens 32 also includes a layer of material 60, which is soluble in the eye, extending from the lens body 34 to the remote portion of the position-fixation means, for example, to the limbs 46, 46 of the position-fixation members 40, 42, thereby stiffening the position-fixation means during insertion thereof into the eye. The layer of material 60 preferably is a layer of at least a component of human blood such as fibrin or the layer may, for example, be coagulated whole human blood. The layer of fibrin is a dry layer which may, for example, be 0.25 mm thick. The layer of material 60 may also be, for example, a layer of gelatin which is dried by exposure to the air, or starch paste made from a mixture of flour and water. The layer of material 60 also may be any other material which is (a) non-toxic and otherwise compatible with the fluid in the human eye, (b) soluble in the fluid in the eye, (c) dryable or otherwise changeable from a liquid state into a semi-rigid or rigid state and capable of adhering to and/or encapsulating the lens for filling the spaces between the optic and the position-fixation members so as to add rigidity to the entire structure.

The layer of material 60 may be applied to the lens 32 by coating the lens with wet material as by brushing, by dipping the lens 32 in wet material thereby encapsulating the lens 32, or by any other suitable technique. The layer of material 60 may then dry on the lens 32 filling the spaces between the optic and the position fixation members and the lens may be inserted into the eye through the opening 58 and seated in the eye by the surgeon. The layer 60 stiffens the position-fixation members 40, 42, facilitating the insertion of the lens into the eye. After the lens is inside the eye the layer of material 60 dissolves naturally in the fluid of the eye and the surgeon may seat the position-fixation members 40, 42 in the eye without need for breaking the layer 60, since the latter will dissolve.

Figure 3:
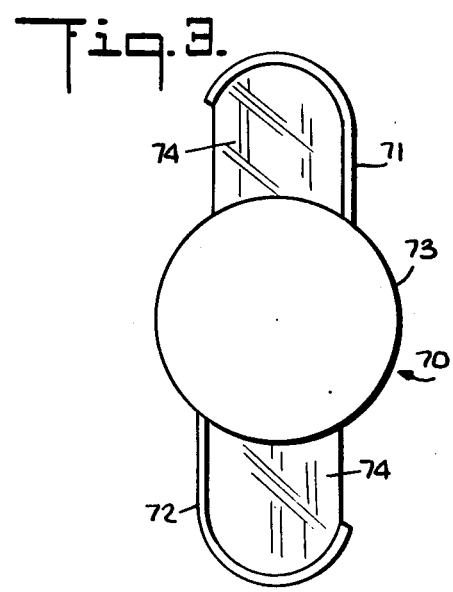
FIG. 3 is a plan view of another embodiment of an intraocular lens constructed in accordance with the invention.

It will be understood that the invention has applications with many other configurations of lenses, for example, the lens 70 represented in FIG. 3. The lens 70 has spindly, curved position-fixation members 71, 72 extending from a lens body or optic 73. A layer of material 74 similar to the material 60 of the FIG. 2 lens may be applied to the FIG. 3 lens to fill the spaces between the optic 73 and the position-fixation members 71, 72. This layer, after it has dried serves to stiffen the lens, as described above, during insertion into and implantation in the eye, but will be dissolved after a time, by the fluid in the eye, so that the position-fixation members will then again exhibit the desired flexibility.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens comprising:
a lens body;
position-fixation means having a first portion extending from said lens body and having a second portion remote from said lens body and extending transversely of said first portion for positioning said lens body within an eye; and
a substantially planar layer of material which is soluble in the eye extending from said lens body to said remote portion of said position-fixation means substantially filling the space therebetween, thereby stiffening said position-fixation means during insertion thereof into the eye.

2. An intraocular lens in accordance with claim 1 in which said first portion of said position-fixation means is a stem portion and in which said remote portion of said position-fixation means is a limb portion having a pair of spaced eye contact portions.

3. An intraocular lens in accordance with claim 2 which includes a pair of stem portions and a pair of limb portions having four spaced eye contact portions.

4. An intraocular lens in accordance with claim 1 in which said layer of material is a layer of at least a component of human blood.

5. An intraocular lens in accordance with claim 4 in which said layer of material is a layer of fibrin.

6. An intraocular lens in accordance with claim 1 in which the material in said layer of material is (a) non-toxic and otherwise compatible with the fluid in the human eye, (b) soluble in the fluid in the eye (c) dryable from a liquid state into a semi-rigid or rigid state and capable of adhering to and/or encapsulating the lens.

7. An intraocular lens comprising:
a lens body;
position-fixation means extending from said lens body and having a portion remote from said lens body for positioning said lens body within an eye; and
a layer of gelatin material which is soluble in the eye extending from said lens body to said remote portion of said position-fixation means, thereby stiffening said position-fixation means during insertion thereof into the eye.

8. A method of positioning an intraocular lens in an eye, the lens comprising a lens body and position-fixation means having a first portion extending from said lens body and having a second portion remote from said lens body and extending transversely of said first portion for positioning said lens body within the eye, comprising:
applying to said lens a substantially planar layer of material which is soluble in the eye extending from said lens body to said remote portion of said position-fixation means for substantially filling the space therebetween to stiffen said lens;
inserting said lens into the eye through an opening in the eye; and
seating said lens in the eye.

9. A method in accordance with claim 8 in which the step of applying to said lens a layer of material comprises applying to said lens a layer of wet material and which includes the step of drying said material to stiffen said lens before insertion thereof into the eye.

10. A method in accordance with claim 8 in which the step of applying to said lens a layer of material comprises applying to said lens a layer of wet material which includes the step of permitting said material to harden to stiffen said lens before insertion thereof into the eye.

* * * * *